United States Patent [19]
Dowd et al.

[11] Patent Number: 5,607,269
[45] Date of Patent: Mar. 4, 1997

[54] BONE MILLING APPARATUS

[75] Inventors: Michael Dowd, Eastampton; Nelson Scarborough, Wayside; Mark Daugherty, Allenwood, all of N.J.

[73] Assignee: Osteotech, Inc., Eatontown, N.J.

[21] Appl. No.: 560,213

[22] Filed: Nov. 21, 1995

[51] Int. Cl.$^6$ .................................................. B23Q 11/08
[52] U.S. Cl. .................................. 409/134; 29/DIG. 56; 29/DIG. 60; 29/DIG. 86
[58] Field of Search ............................ 409/134; 606/80, 606/96; 160/218, 219; 74/18, 18.1, 566; 29/DIG. 56, DIG. 60, DIG. 86

[56] References Cited

U.S. PATENT DOCUMENTS

| | | | |
|---|---|---|---|
| 3,669,459 | 6/1972 | Bass | 277/174 |
| 3,856,219 | 12/1974 | Stayton et al. | 241/263 |
| 4,126,081 | 11/1978 | Zdeb . | |
| 4,162,647 | 7/1979 | Aslen . | |
| 4,242,019 | 12/1980 | Roch . | |
| 4,514,936 | 5/1985 | Hurtado | 451/28 |
| 4,565,915 | 1/1986 | Girardin | 219/69 W |
| 4,742,609 | 5/1988 | Neumann | 409/135 |
| 4,834,596 | 5/1989 | Hollifield et al. | 409/232 |
| 4,884,927 | 12/1989 | Menker . | |
| 5,117,880 | 6/1992 | Kapton et al. . | |
| 5,181,898 | 1/1993 | Piotrowski | 409/134 |
| 5,298,254 | 3/1994 | Prewett et al. . | |
| 5,439,431 | 8/1995 | Hessbruggen et al. | 409/134 |
| 5,449,256 | 9/1995 | Sundman | 409/134 |
| 5,482,414 | 1/1996 | Hayashi et al. | 409/134 |

*Primary Examiner*—M. Rachuba
*Assistant Examiner*—Christopher Kirkman
*Attorney, Agent, or Firm*—Dilworth & Barrese

[57] ABSTRACT

A milling apparatus is disclosed which includes a milling machine having a milling cutter which is sealingly isolated from the milling machine within an enclosed work area, a support fixture disposed within the enclosed work area for supporting a work piece, and a mechanism for moving the milling cutter along a predetermined path relative to the work piece. Preferably, the milling apparatus is employed to cut bone into small fragments for subsequent utilization, and the sealed isolation of the milling cutter inhibits cross-contamination between differing work pieces.

16 Claims, 7 Drawing Sheets

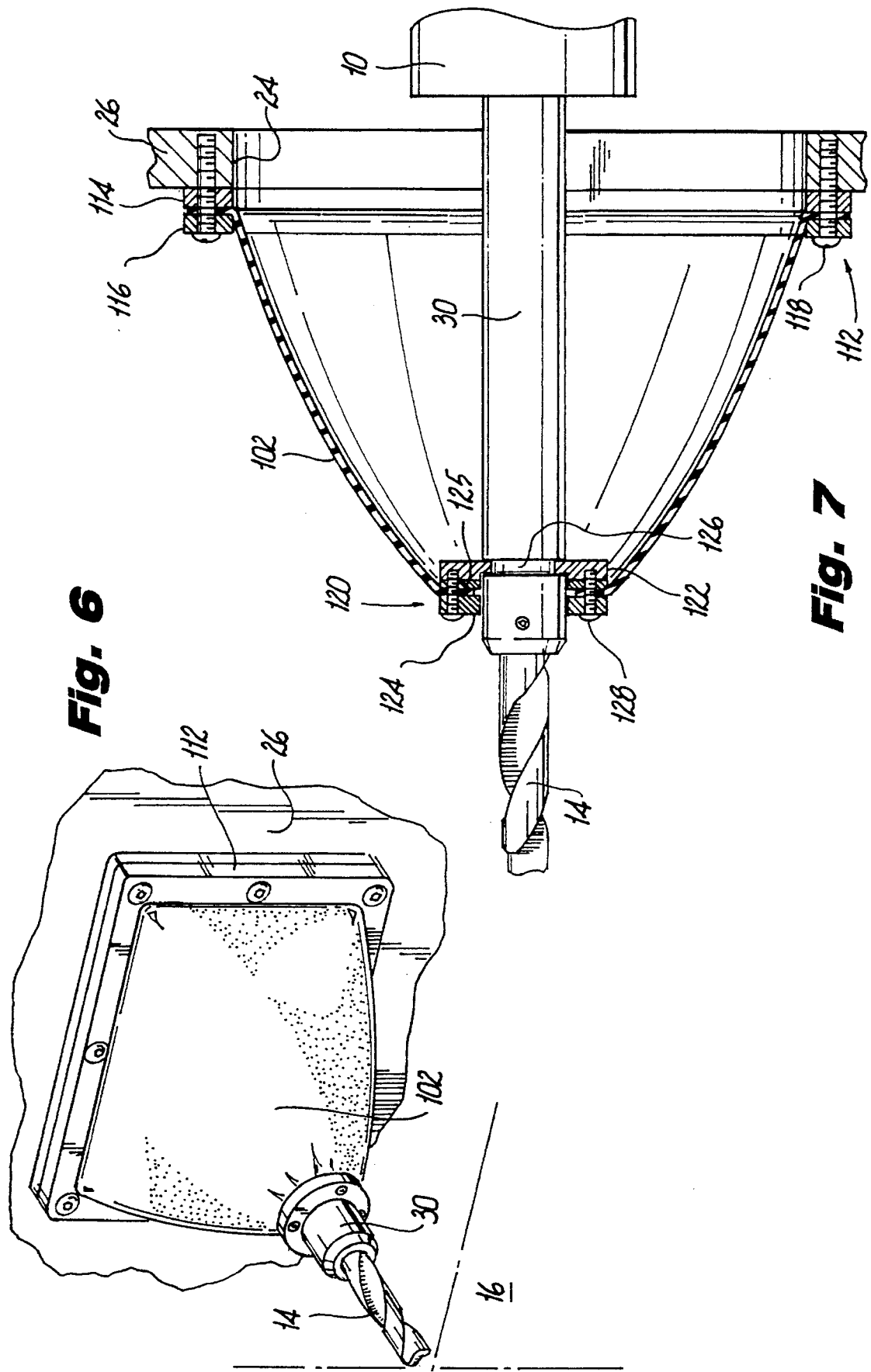

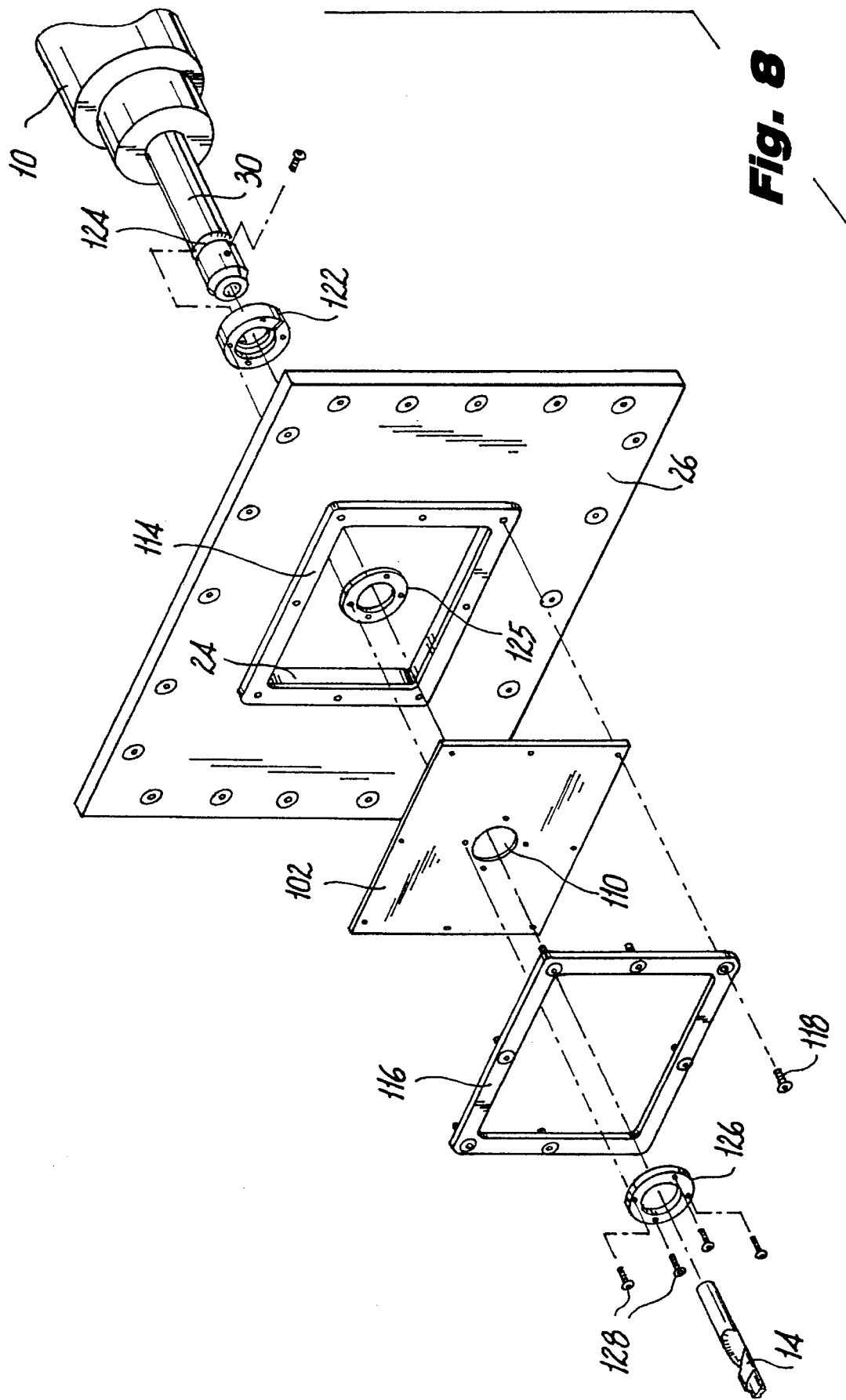

BONE MILLING APPARATUS

BACKGROUND OF THE INVENTION

1. Field of the Invention

This invention relates to an apparatus for cutting bone, and more particularly, to an apparatus for milling bone fragments which are subsequently demineralized and used to produce shaped materials.

2. Description of the Related Art

The use of demineralized bone fragments in the repair of bone defects and construction of shaped osteogenic materials such as sheets, plates, disks, pins, and the like has been known for some time. Shaped materials formed from pieces of demineralized bone and a method for forming such materials are disclosed in commonly assigned U.S. Pat. No. 5,298,254 to Prewett et al. The bone pieces utilized to form these shaped materials are preferably cut or machined to a desired size and dimension, with the geometry of the pieces being substantially regular in configuration.

A preferred method of machining or cutting bone fragments involves the use of a milling machine having a rotating cutter which produces substantially uniform bone fragments. Conventional prior art milling machines such as those disclosed, for example, in U.S. Pat. No. 4,242,019 to Roch, and U.S. Pat. No. 5,117,880 to Kapton et al. are not well suited for such a task however, since the working parts of these machines are not separated or isolated from the work area in which the bone fragments are produced. As a result, bone fragments produced from one piece of bone during a particular milling operation may become associated with the working parts of the machine, causing cross-contamination with bone fragments produced from another piece of bone in a subsequent milling operation.

It would be desirable therefore, to provide a milling machine in which the milling cutter and work area are isolated or separated from the working parts of the milling machine so that cross-contamination between differing work pieces can be prevented.

SUMMARY OF THE INVENTION

The subject invention is directed to a milling apparatus which includes a milling machine having a milling cutter which is sealingly isolated from the milling machine within an enclosed work area. The work area is preferably separated from the milling machine by an upstanding wall having a portal formed therein for accommodating the milling cutter. A support fixture is disposed within the work area for supporting a work piece adjacent the milling cutter, and means are provided for moving the milling cutter relative to the work piece. The subject invention further includes sealing means which are operatively associated with the portal for sealingly isolating the milling cutter and the work area from the milling machine.

In one preferred embodiment of the subject invention, the sealing means comprises a sealing plate which is slidably mounted adjacent the portal and which has an aperture extending therethrough for receiving a chuck which supports the milling cutter. The sealing plate is secured to a flange which is operatively associated with the chuck, and it is disposed adjacent an exterior surface of the upstanding wall. A support plate maintains the sealing plate in this position while permitting the slidable movement thereof. Preferably, a first sheet of self-lubricating material is disposed between the sealing plate and the exterior surface of the upstanding wall and a second sheet of self-lubricating material is disposed between the sealing plate and the support plate.

In another preferred embodiment of the subject invention, the sealing means comprises a sealing boot constructed of a flexible material which is mounted adjacent the portal and which has an aperture extending therethrough for receiving the chuck which supports the milling cutter. A first flange assembly is disposed about the periphery of the portal for sealingly securing the sealing boot to an interior surface of the upstanding wall, and a second flange assembly is disposed about the chuck for sealingly securing the sealing boot thereto.

In a preferred embodiment of the subject invention, the milling apparatus is particularly adopted for bone cutting and includes a milling machine having a milling cutter, an enclosed work area separated from the milling machine into which the milling cutter extends from the milling machine, a support fixture disposed within the work area for supporting a work piece consisting of a piece of bone adjacent the milling cutter, means for moving the milling cutter along a predetermined path with respect to the work piece to produce bone fragments for subsequent utilization, and sealing means for sealingly isolating the milling cutter from the milling machine so that bone fragments produced by the milling cutter are inhibited from associating with the milling machine, thereby preventing cross-contamination between differing work pieces. In addition, a catchment basin is disposed within the enclosed work area for collecting the bone fragments produced by the milling cutter.

These and other features of the bone milling apparatus of the subject invention will become more readily apparent to those skilled in the art from the following detailed description of the invention taken in conjunction with the drawings.

BRIEF DESCRIPTION OF THE DRAWINGS

So that one skilled in the art to which the subject invention appertains will better understand how to make and use the bone milling apparatus of the subject invention, preferred embodiments thereof will be described hereinbelow with reference to the drawings wherein:

FIG. 6 is a perspective view of a flexible sealing boot assembly utilized to sealingly isolate the milling cutter and the enclosed work area from the milling machine;

FIG. 7 is a cross-sectional view of the flexible sealing boot assembly of FIG. 6 with the flange connections associated therewith clearly illustrated;

FIG. 8 is an exploded perspective view of the sealing boot assembly of FIG. 6 and the flanges which connect the boot to the chuck of the milling machine and the interior wall which separates the work area from the milling machine;

DETAILED DESCRIPTION OF THE PREFERRED EMBODIMENTS

Figure 1:
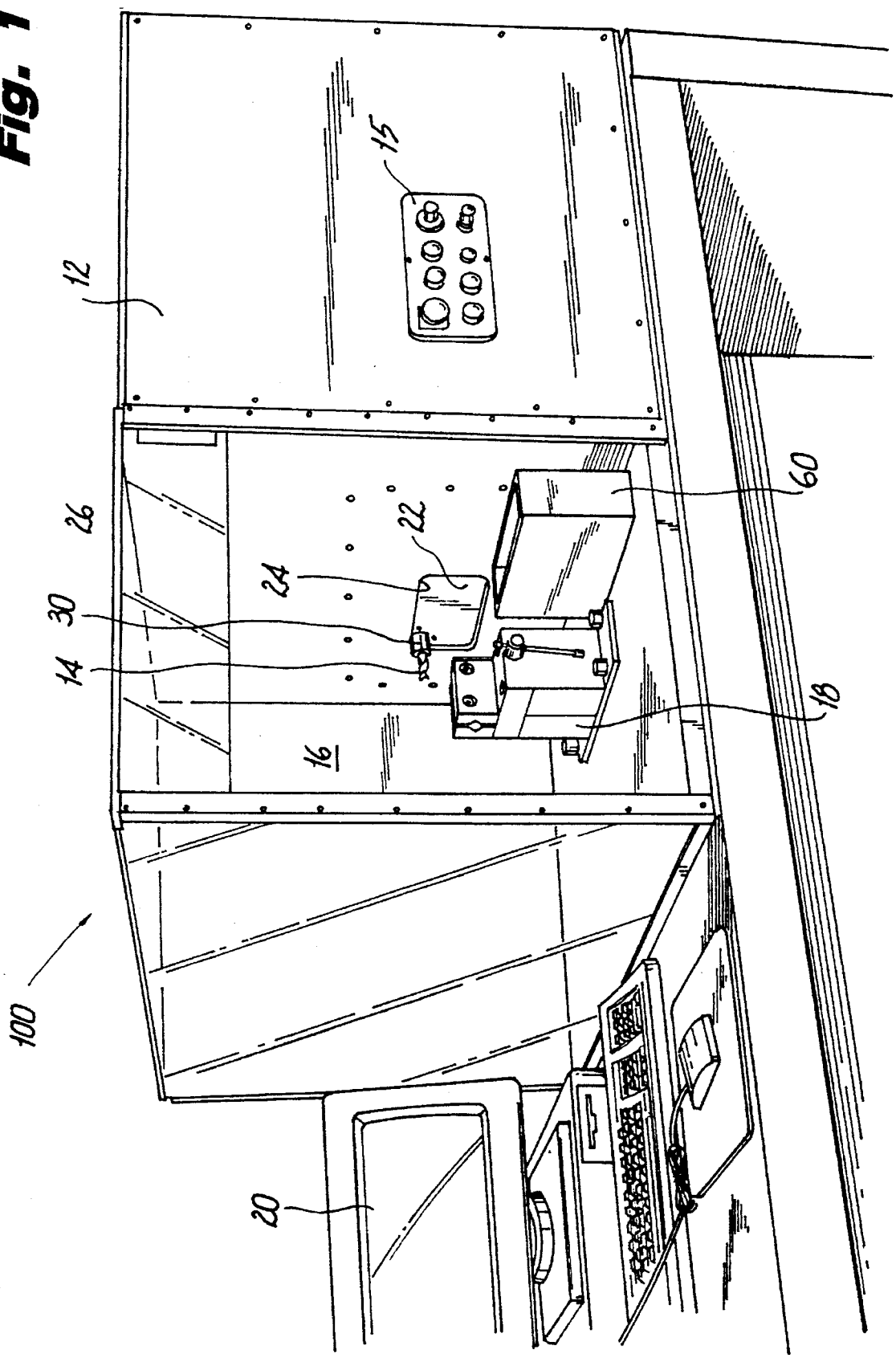
FIG. 1 is a perspective view of a work station employing a bone milling apparatus constructed in accordance with a preferred embodiment of the subject invention.

Referring now to the drawings wherein like reference numerals identify similar structural elements or components of the subject invention, there is illustrated in FIG. 1 a workstation which employs a bone milling apparatus constructed in accordance with a preferred embodiment of the subject invention and designated generally by reference numeral 100.

Figure 2:
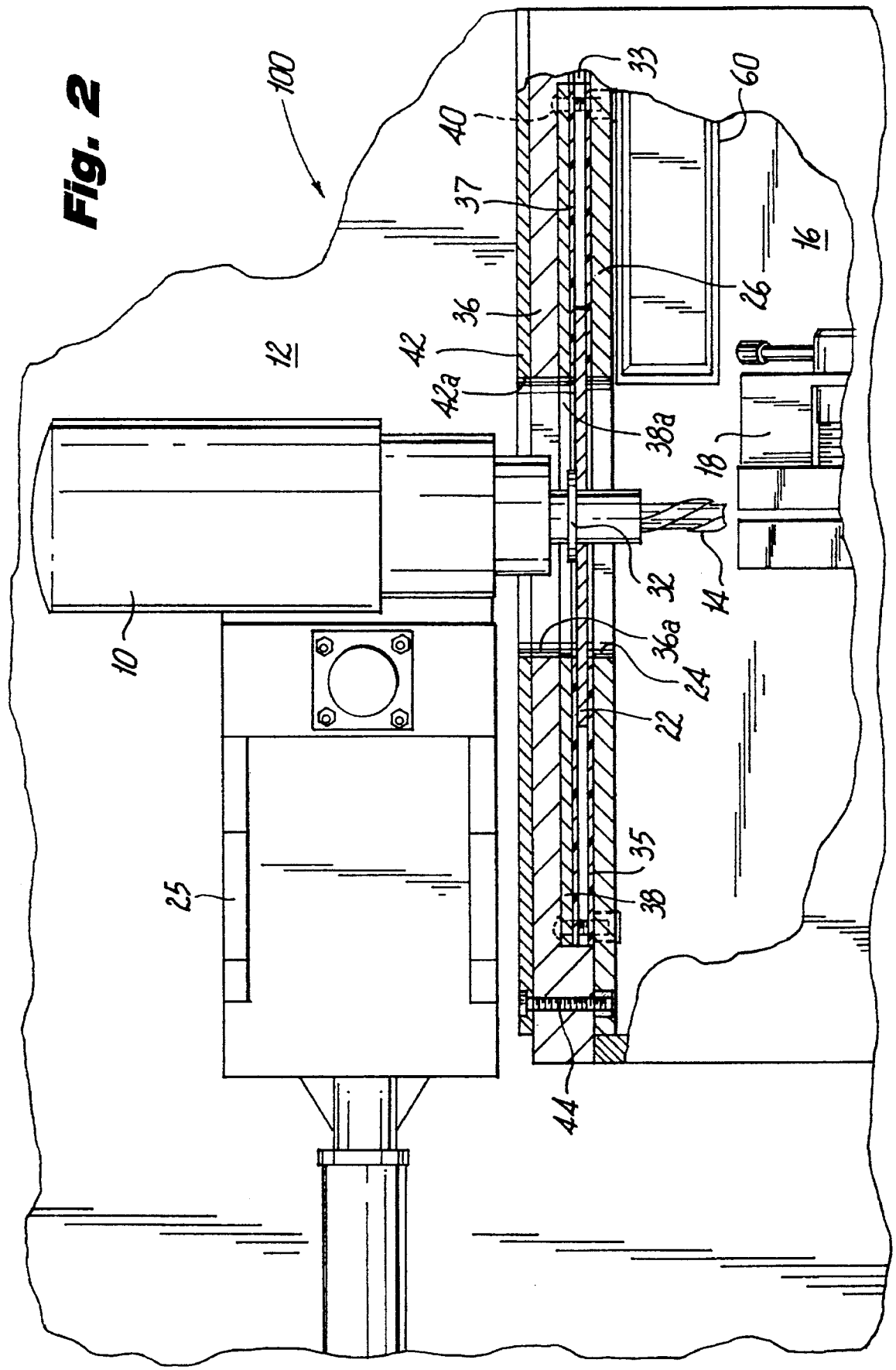
FIG. 2 is a top plan view of the bone milling apparatus of FIG. 1 with the wall of the enclosed work area shown in cross-section to illustrate the slidably mounted sealing plate arrangement which isolates the milling cutter and the work area from the milling machine.

Referring to FIGS. 1 and 2, milling apparatus 100 includes a milling machine 10 housed within an enclosure 12. Milling machine 10 has a conventional variable speed motor, and a control panel 15 is provided on enclosure 12 to facilitate user operation of the milling machine. The panel includes a plurality of switches which control, among other things, motor start, spindle speed, shut-down and emergency stop. Milling machine 10 includes a milling cutter 14 in the form of a fluted milling tip which extends from enclosure 12 into an enclosed work area 16 in which bone milling operations are performed. Although the enclosed work area illustrated in FIG. 1 is a small cabinet, it is envisioned and within the scope of the subject invention that the enclosed work area could be as large as a room, and the milling cutter would extend into the room from an adjacent room.

In accordance with the subject invention, the workpiece and the milling cutter are advantageously situated within the enclosed work area 16, isolated from milling machine 10, so that cross-contamination between different workpieces is avoided. Moreover, bone fragments produced from a piece of demineralized bone during a milling operation will remain in the enclosed work area and will be unable to associate with the working parts of the milling machine. Accordingly, bone fragments produced from other pieces of bone during subsequent milling operations will not become contaminated. Furthermore, the milling machine will remain free from debris which could effect its operation and make cleaning somewhat difficult. In addition, if it becomes desirable to maintain the workpiece in a sterile environment, isolating and sealing the working parts of the milling machine from the enclosed work area becomes extremely advantageous.

A support fixture 18 in the form of a conventional work holding vise with movable jaws is disposed within work area 16 for supporting a workpiece (i.e., a piece of bone shaft) adjacent milling cutter 14. A conventional linear drive assembly 25 is also associated with the milling machine. Linear drive assembly 25 is controlled by computer system 20 and is configured to move the milling cutter 14 along a predetermined path with respect to the workpiece during a milling operation.

Figure 3:
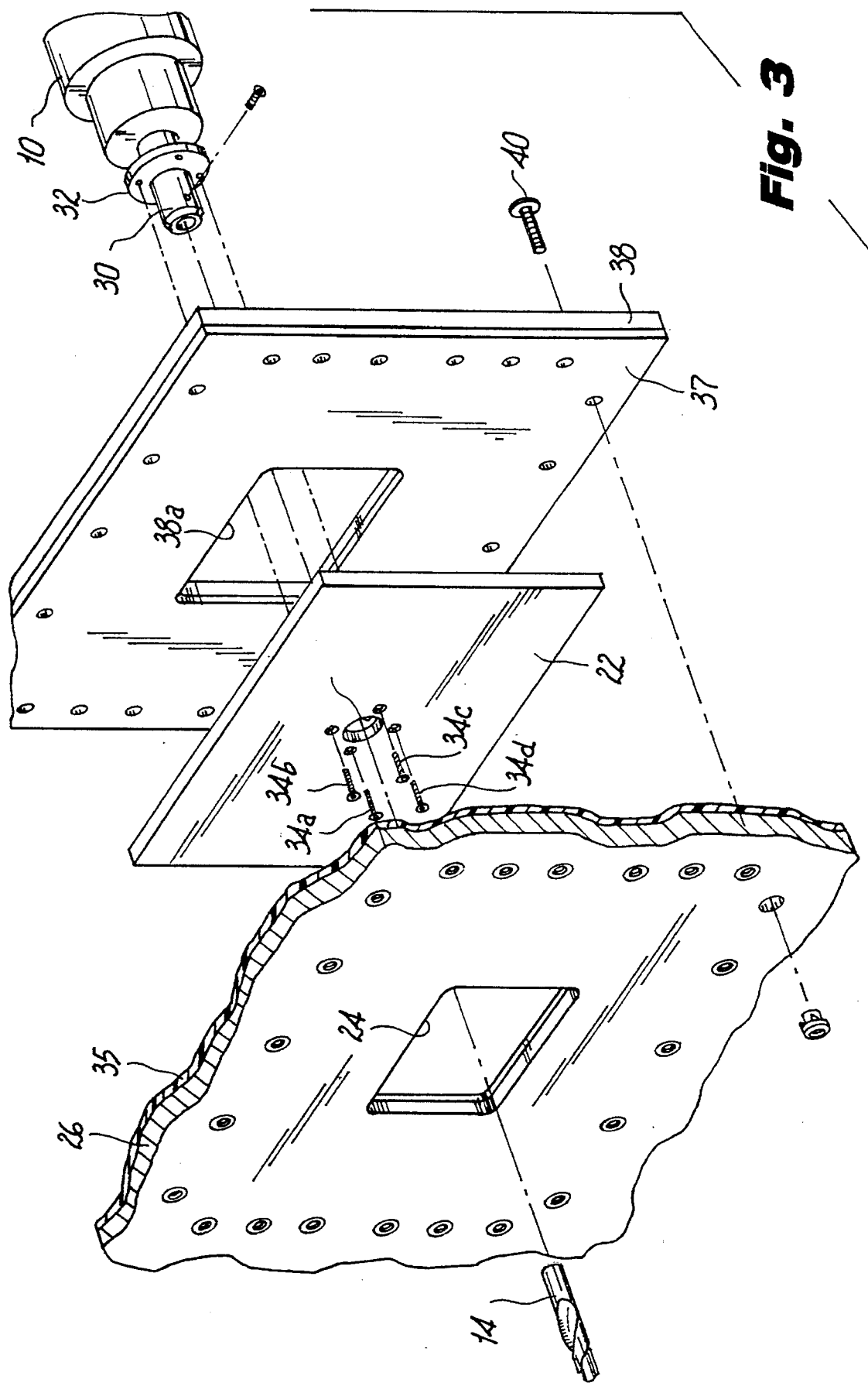
FIG. 3 is an exploded perspective view of the sealed portion of the wall which separates the enclosed work area from the milling machine in the apparatus illustrated in FIG. 1.

Referring to FIGS. 2 and 3, the sealed isolation of milling machine 10 from milling cutter 14 and enclosed work area 16 is achieved by way of a movable sealing plate 22. Sealing plate 22 is mounted adjacent a portal 24 formed in the upstanding wall 26 of the enclosed work area 16 and is provided with an aperture 28 through which the rotating chuck 30 of milling machine 10 extends. A flange 32 is positioned on chuck 30 in a manner which permits rotation of the chuck relative to the flange. A plurality of fasteners 34a–34d mount sealing plate 22 to chuck 30. Thus, when chuck 30 translates in an x–y plane in response to the movement of milling machine 10 by the linear drive assembly 25, sealing plate 22 translates with respect to portal 24 within a sealed cavity 33 defined within the retaining wall 36 of enclosure 12.

More particularly, as best seen in FIG. 2, sealing plate 22 is disposed between the rear surface of upstanding wall 26 and a surface of support plate 38 which is secured within sealed cavity 33 by a plurality of fasteners 40. Self-lubricating sheets of material 35 and 37, preferably formed from Teflon®, line the beating surfaces of support plate 38 and upstanding wall 26 to reduce the frictional contact between the sealing plate 22 and the beating surfaces. An enlarged mounting plate 42 is positioned against retaining wall 36, within enclosure 12, to facilitate the securement of upstanding wall 26 to retaining wall 36 via a plurality of threaded fasteners 44. Portals 36a, 38a and 42a are provided in retaining wall 36, support plate 38 and mounting plate 42, respectively, to accommodate the translation of chuck 30 as it moves within an x–y plane. These portals are dimensioned and configured to match the geometry of the portal 24 provided in the upstanding wall 26 of the enclosed work area.

Figure 4:
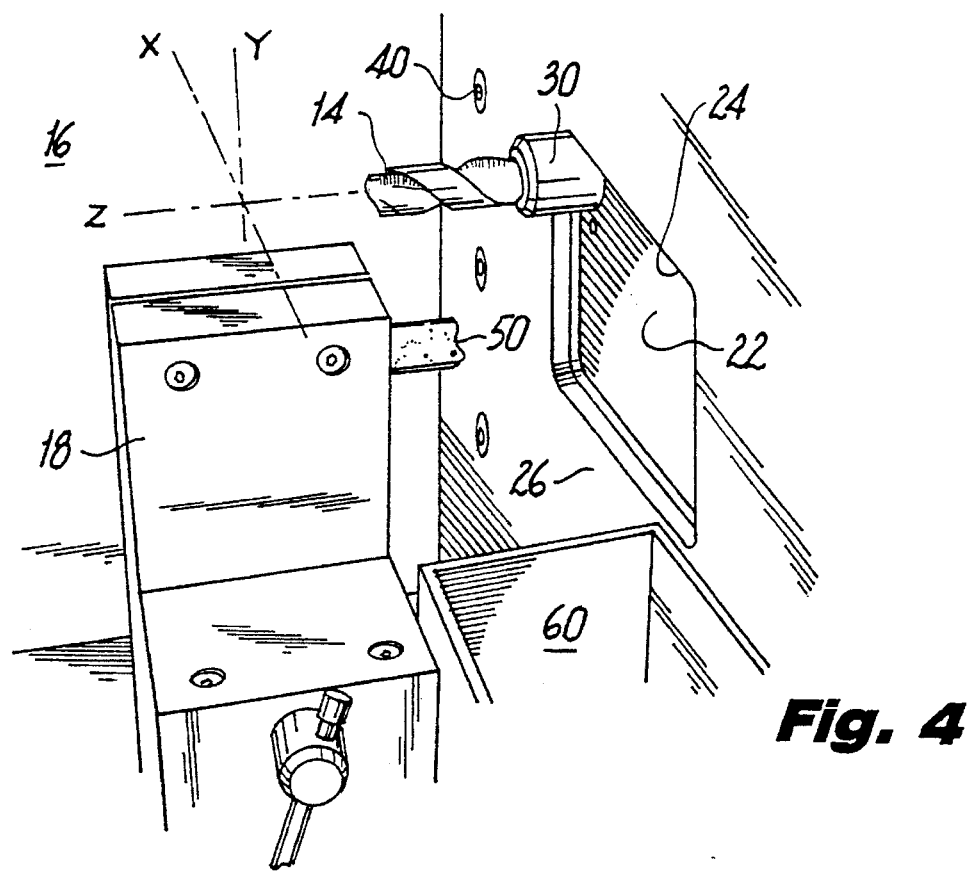
FIG. 4 is a perspective view of the milling cutter in a home position isolated within the enclosed work area of the work station prior to a bone milling operation involving a piece of demineralized bone maintained in the support fixture of the milling apparatus.
Figure 5:
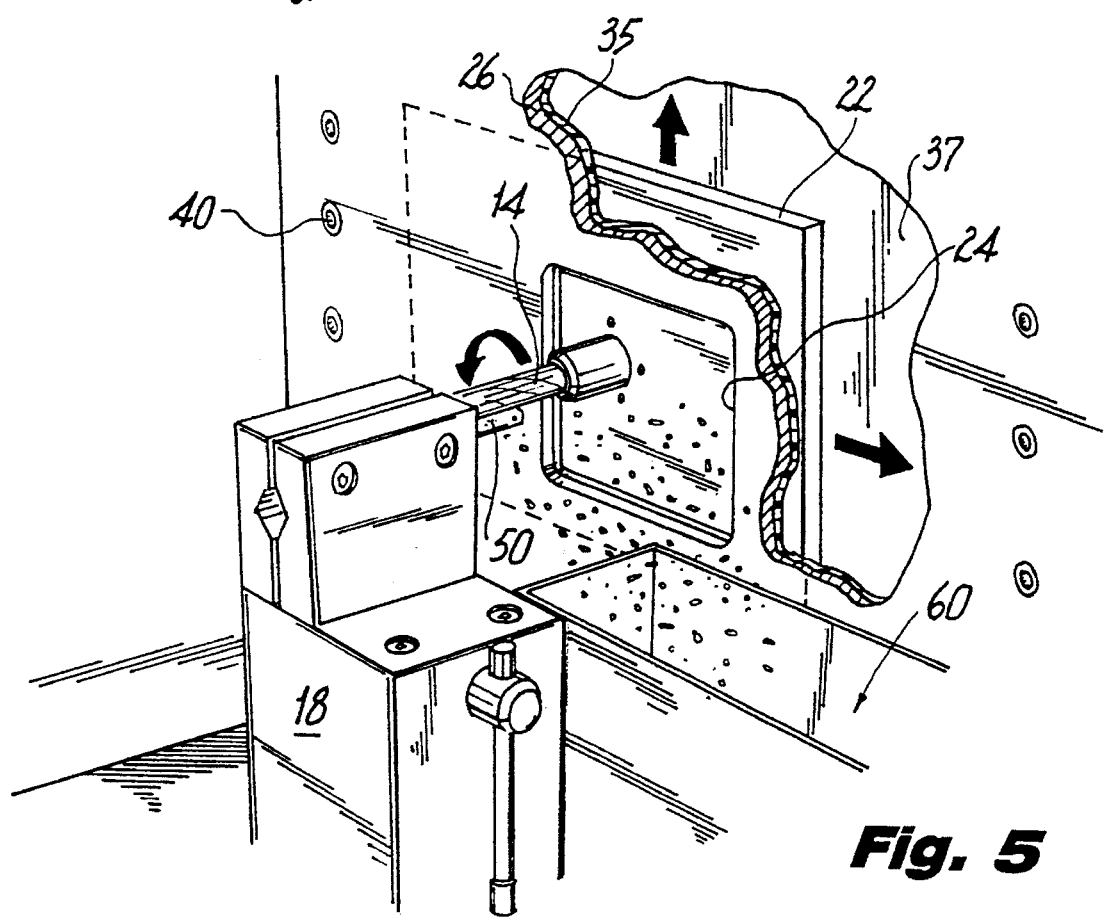
FIG. 5 is a perspective view of the milling cutter in operation as fragments of bone are cut and collected within a catchment basin disposed in the enclosed work area.

Turning now to FIG. 4, in operation, prior to a bone milling operation, a piece of bone designated by reference numeral 50 is positioned within the jaws of support fixture 18 adjacent milling cutter 14. At such a time, milling cutter 14 is in a pre-operating home position located in the upper left-hand corner of portal 24. Initially, the operator of workstation 100 engages the milling machine by actuating an appropriate control switch on the front panel 15 of enclosure 12. Thereupon, the spindle drive of milling machine 10 begins to rotate chuck 30 and milling cutter 14. When the milling cutter is rotating at a desired speed, computer system 20 engages linear drive assembly 25 and it begins to move milling cutter 14 relative to the piece of demineralized bone 50 along a predetermined path which has been programmed into the computer system. Preferably, the milling cutter makes consecutive passes against the piece of bone, producing a plurality of shavings or fragments each having a generally uniform geometry, as illustrated in FIG. 5. As the fragments of bone are produced, they are collected in a catchment basin 60 which is disposed against upstanding wall 26 within enclosed work area 16. After the milling operation, catchment basin 60 is removed from the work area and the fragments are transferred to a processing area wherein they are utilized to produce shaped osteogenic materials.

Referring now to FIG. 6, there is illustrated another embodiment of a sealing assembly which isolates the enclosed work area 16 and milling cutter 14 from the working parts of milling machine 10 disposed within enclosure 12. As best seen in FIG. 7, this sealing assembly includes a flexible sealing boot 102 constructed from a sheet of latex, or a similar material. The sheet has a centrally located aperture 110 for receiving and accommodating the rotating chuck 30 of milling machine 10. The latex sheet which forms sealing boot 102 is mounted adjacent the portal 24 in upstanding wall 26 by a peripheral flange assembly 112 which includes a gasket flange 114 and a mounting flange 116. The outer periphery of the latex sheet is secured between gasket flange 114 and mounting flange 116, and the entire assembly is mounted to upstanding wall 26 by a plurality of threaded fasteners 118.

Referring to FIGS. 7 and 8, a second flange assembly 120 is provided to sealingly secure the sheet of latex material which forms sealing boot 102 to the chuck 30 adjacent the distal end thereof. Flange assembly 120 includes an annular mounting flange 122 which is supported in an annular groove 124 defined in chuck 30 in a manner which permits rotation of the chuck with respect to the sealing boot. Flange assembly 120 further includes an annular gasket flange 126 which is fastened to mounting flange 122 by a plurality of threaded fasteners 128. A washer 125 is positioned between mounting flange 122 and gasket flange 124. The latex material located adjacent the periphery of aperture 110 is sealingly secured between gasket flange 126 and mounting flange 122. Flange assemblies 112 and 120 are designed so that the flexible sealing boot may be easily removed and replaced when it becomes desirable to do so. In operation, when chuck 30 translates with the linear drive assembly 25 along a predetermined cutting path with respect to a work piece, sealing boot 102 flexes and complies with this movement maintaining the work area in sealed isolation.

Figure 10:
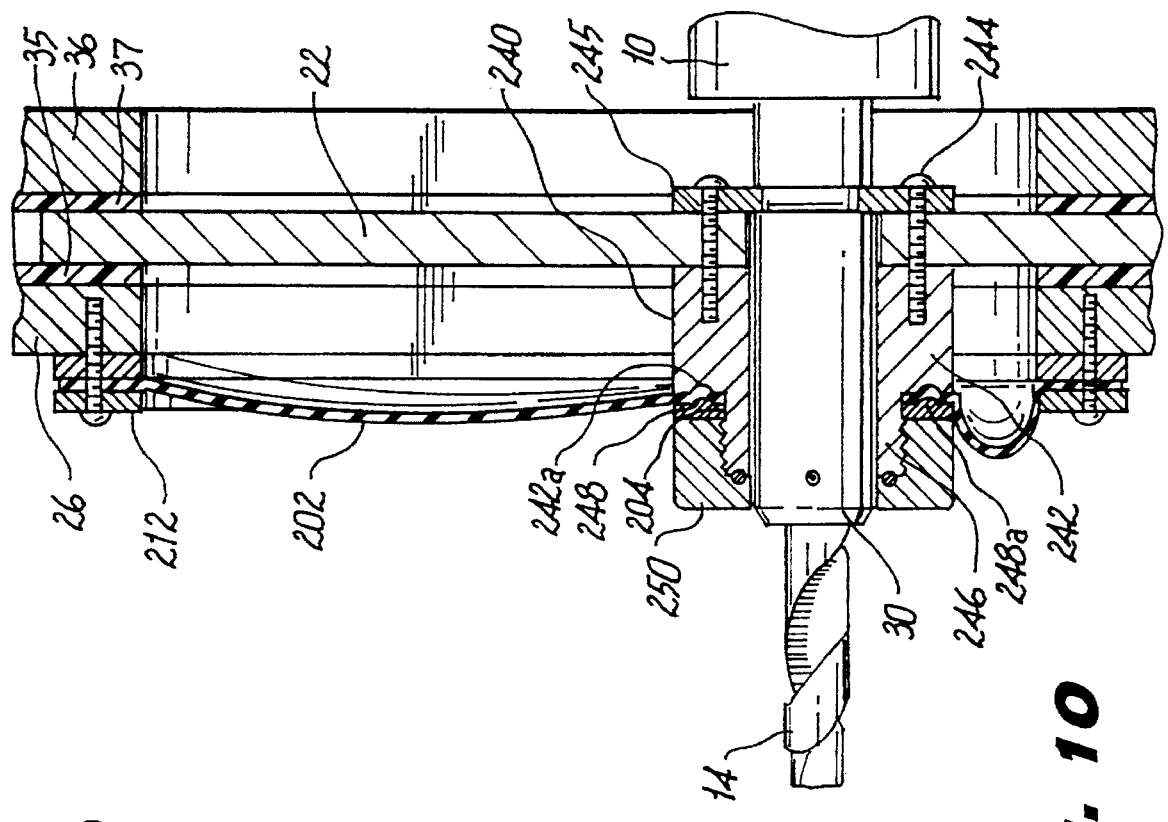
FIG. 10 is a cross-sectional view of the flexible sealing boot assembly of FIG. 9 with the flange connections associated therewith clearly illustrated.
Figure 9:
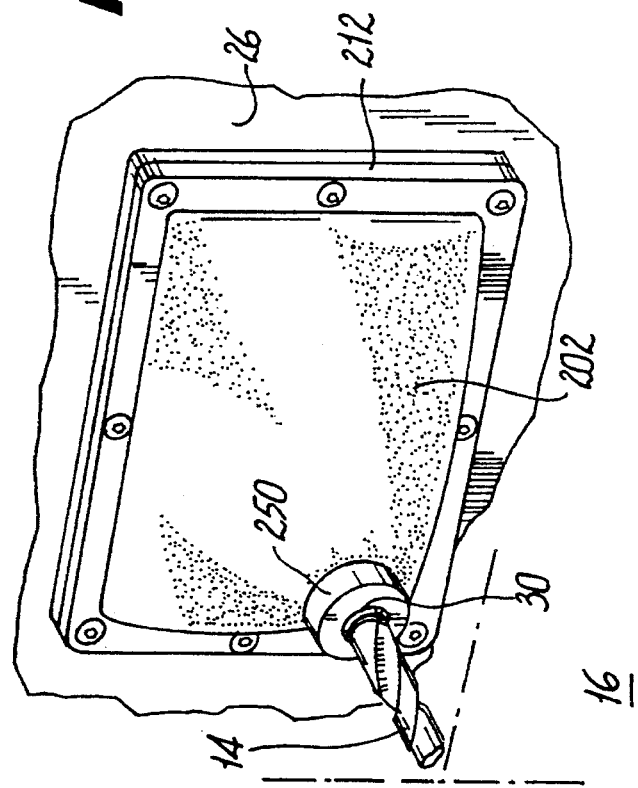
FIG. 9 is a perspective view of another flexible sealing boot assembly utilized to sealingly isolate the milling cutter and the enclosed work area from the milling machine.

Referring now to FIGS. 9–10, there is illustrated another embodiment of a sealing assembly configured to isolate the enclosed work area 16 and the milling cutter 14. As in the previously described embodiment shown in FIGS. 6–8, the sealing assembly of FIGS. 9–10 includes a flexible sealing boot 202 having an aperture 204 for accommodating chuck 30, and a flange arrangement 212 for mounting the outer periphery of the sealing boot to upstanding wall 26. The later sealing assembly differs from the former in that it includes a stepped hub 240 for mounting sealing boot 202 adjacent the distal end portion of chuck 30. Hub 240 has axial bore extending therethrough for accommodating chuck 30 and includes a base portion 242 secured to sealing plate 22 by a plurality of threaded fasteners 244 and a retention flange 245, and further includes a threaded extension portion 246 dimensioned to receive a ribbed compression washer 248 and a threaded mounting nut 250. The rib 248a on compression washer 248 is configured to cooperate with an annular recess 242a defined in the base portion 242 of hub 240, and more particularly, rib 248a urges an annular section of sealing boot 202 into recess 242a to sealing secure the boot adjacent the distal end of portion of chuck 30.

Although the subject invention has been described with respect to preferred embodiments, it will be readily apparent to those having ordinary skill in the art to which it appertains that changes and modifications may be made thereto without departing from the spirit or scope of the subject invention as defined by the appended claims.

What is claimed is:

1. Milling apparatus comprising:
 a) a milling machine and a milling cutter;
 b) a support fixture disposed within an enclosed work area for supporting a work piece;
 c) means for moving the milling cutter relative to the work piece;
 d) an upstanding wall having a portal, the milling cutter extending through and being movable throughout the planar region defining the portal; and
 e) sealing means operatively associated with the portal for sealingly isolating the milling cutter from the milling machine;
 wherein the sealing means comprises a sealing plate slidably mounted adjacent the portal and having an aperture extending therethrough for receiving a chuck which supports the milling cutter, the sealing plate being mounted to a flange provided on the chuck.

2. Milling apparatus as recited in claim 1, wherein the sealing plate is disposed adjacent an exterior surface of the upstanding wall and a support plate maintains the sealing plate in such position while permitting slidable movement thereof.

3. Milling apparatus as recited in claim 2, wherein a first sheet of self-lubricating material is disposed between the sealing plate and the exterior surface of the upstanding wall and a second sheet of self-lubricating material is disposed between the sealing plate and the support plate.

4. Milling apparatus comprising
 a) a milling machine and a milling cutter, the milling cutter being positioned within an enclosed work area, the work area being separated from the milling machine by a fixed upstanding wall having a portal formed therein for accommodating the milling cutter;
 b) a support fixture disposed within the work area for supporting a work piece adjacent the milling cutter;
 c) means for moving the milling cutter throughout the planar region defining the portal and relative to the work piece; and
 d) sealing means operatively associated with the portal for sealingly isolating the milling cutter and work area from the milling machine
 wherein the sealing means comprises a sealing plate sized to cover the entire portal, the sealing plate being slidably mounted adjacent the portal and having an aperture extending therethrough for receiving a chuck which supports the milling cutter, the sealing plate being mounted to a flange provided on the chuck.

5. Milling apparatus as recited in claim 4, wherein the sealing plate is disposed adjacent an exterior surface of the upstanding wall and a support plate maintains the sealing plate in such position while permitting slidable movement thereof.

6. Milling apparatus as recited in claim 16, wherein a first sheet of self-lubricating material is disposed between the sealing plate and the exterior surface of the upstanding wall and a second sheet of self-lubricating material is disposed between the sealing plate and the support plate.

7. Bone milling apparatus comprising:
 a) a milling machine and a milling cutter;
 b) an enclosed work area separated from the milling machine by an isolation wall having a portal, the milling cutter extending through the portal into the work area from the milling machine;
 c) a support fixture disposed within the work area for supporting a work piece consisting of bone adjacent the milling cutter;
 d) means for moving the milling cutter throughout the planar region defining the portal along a predetermined path with respect to the work piece to produce bone fragments for subsequent utilization; and
 e) a sealing member operatively associated with the portal, the sealing member isolating the milling cutter from the milling machine so that bone fragments produced by the milling cutter are inhibited from contacting the milling machine, thereby preventing cross-contamination between differing work pieces;
 wherein the sealing member comprises a single sealing plate slidably mounted adjacent to and covering the portal and having an aperture extending therethrough for receiving a chuck which supports the milling cutter, the sealing plate being mounted to a flange provided on the chuck.

8. Bone milling apparatus as recited in claim 7, further comprising a catchment basin disposed within the enclosed work area for collecting the bone fragments produced by the milling cutter.

9. Bone milling apparatus as recited in claim 7, wherein the sealing plate is disposed adjacent an exterior surface of the upstanding wall and a support plate maintains the sealing plate in such position while permitting slidable movement thereof.

10. Milling apparatus comprising:
   a) a milling machine and a milling cutter;
   b) a support fixture disposed within an enclosed work area for supporting a work piece;
   c) means for moving the milling cutter relative to the work piece;
   d) an upstanding wall having a portal, the milling cutter extending through and being movable transversely and vertically throughout a planar region defining the portal; and
   e) sealing means operatively associated with the portal for sealingly isolating the milling cutter from the milling machine;
   wherein the sealing means comprises a sealing boot constructed of a flexible material mounted adjacent the portal and having an aperture extending therethrough for receiving a chuck which supports the milling cutter, the sealing boot being mounted to a flange provided on the chuck.

11. Milling apparatus as recited in claim 10, further comprising a flange assembly disposed about the periphery of the portal for sealingly securing the sealing boot to an interior surface of the upstanding wall.

12. Milling apparatus as recited in claim 10, wherein the sealing boot is constructed from a sheet of latex material.

13. Milling apparatus comprising:
   a) a milling machine and a milling cutter, the milling cutter being positioned within an enclosed work area, the work area being separated from the milling machine by a fixed upstanding wall having a portal formed therein for accommodating the milling cutter;
   b) a support fixture disposed within the work area for supporting a work piece adjacent the milling cutter;
   c) means for moving the milling cutter transversely and vertically throughout a planar region defining the portal and relative to the work piece; and
   d) sealing means operatively associated with the portal for sealingly isolating the milling cutter and work area from the milling machine;
   wherein the sealing means comprises a sealing boot constructed of a flexible material mounted adjacent the portal and having an aperture extending therethrough for receiving a chuck which supports the milling cutter, the sealing boot being mounted to a flange provided on the chuck.

14. Milling apparatus as recited in claim 13, further comprising a flange assembly disposed about the periphery of the portal for sealingly securing the sealing boot to an interior surface of the upstanding wall.

15. Bone milling apparatus comprising:
   a) a milling machine and a milling cutter;
   b) an enclosed work area separated from the milling machine by an isolation wall having a portal, the milling cutter extending through the portal into the work area from the milling machine;
   c) a support fixture disposed within the work area for supporting a work piece consisting of bone adjacent the milling cutter;
   d) means for moving the milling cutter transversely and vertically throughout a planar region defining the portal along a predetermined path with respect to the work piece to produce bone fragments for subsequent utilization; and
   e) a sealing member operatively associated with the portal, the sealing member isolating the milling cutter from the milling machine so that bone fragments produced by milling cutter are inhibited from contact the milling machine, thereby preventing cross-contamination between differing work pieces;
   wherein the sealing member comprises a sealing boot constructed of a flexible material mounted adjacent the portal and having an aperture extending therethrough for receiving a chuck which supports the milling cutter, the sealing boot being mounted to a flange provided on the chuck.

16. Bone milling apparatus as recited in claim 15, further comprising a flange assembly disposed about the periphery of the portal for sealingly securing the sealing boot to an interior surface of the upstanding wall.

* * * * *